(12) United States Patent
Bodhuri et al.

(10) Patent No.: US 8,765,976 B2
(45) Date of Patent: Jul. 1, 2014

(54) POLYMORPHIC FORMS OF WARFARIN POTASSIUM AND PREPARATIONS THEREOF

(75) Inventors: Prabhudas Bodhuri, Brantford (CA); Gamini Weeratunga, Ancaster (CA); Keshava K. S. Murthy, Ancaster (CA)

(73) Assignee: Apotex Pharmachem Inc., Brantford (CA)

( * ) Notice: Subject to any disclaimer, the term of this patent is extended or adjusted under 35 U.S.C. 154(b) by 0 days.

(21) Appl. No.: 13/699,293

(22) PCT Filed: May 20, 2011

(86) PCT No.: PCT/CA2011/000572
§ 371 (c)(1),
(2), (4) Date: Feb. 4, 2013

(87) PCT Pub. No.: WO2011/143747
PCT Pub. Date: Nov. 24, 2011

(65) Prior Publication Data
US 2013/0143957 A1 Jun. 6, 2013

Related U.S. Application Data

(60) Provisional application No. 61/346,680, filed on May 20, 2010.

(51) Int. Cl.
*C07D 311/02* (2006.01)
(52) U.S. Cl.
USPC ........................................................ 549/286
(58) Field of Classification Search
USPC ........................................................ 549/286
See application file for complete search history.

*Primary Examiner* — Nizal Chandrakumar

(57) ABSTRACT

There is provided crystalline solvate forms of Warfarin potassium, termed APO-I and APO-II, and processes for making APO-I and APO-II. APO-I and APO-II are polymorphic solvate forms of Warfarin potassium.

7 Claims, 6 Drawing Sheets

POLYMORPHIC FORMS OF WARFARIN POTASSIUM AND PREPARATIONS THEREOF

TECHNICAL FIELD

The present invention relates to polymorphic forms of Warfarin Potassium and processes for its preparation.

BACKGROUND

Warfarin potassium (1) is an anticoagulant and it is marketed in USA under the commercial name Athrombin-K™. Chemically, Warfarin potassium is monopotassium (RS)-2-oxo-3-(3-oxo-1-phenylbutyl)-chromen-4-olate. Warfarin is also known in the literature to exist as the Warfarin acid and Warfarin alkali metal salts such as sodium and lithium. Warfarin is marketed in the United States as Coumadin™ and Jantoven™. It is also marketed outside the United States as Marevan™, Lawarin™, and Waran™. Warfarin and Warfarin-alkali metal derivatives are also commonly used as rodenticides.

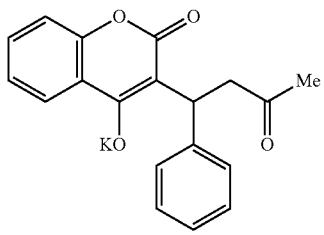

Warfarin Potassium (1)

U.S. Pat. No. 2,765,321 discloses a process of making crystalline Warfarin sodium.

U.S. Pat. No. 2,777,859 discloses Warfarin-alkali metal derivatives and processes of preparing the same.

U.S. Pat. No. 3,077,481 (re issued as RE25866) discloses that when Warfarin sodium is in solution in A. R. isopropyl alcohol ($C_3H_7OH$, B. P. 82.4° C.), the Warfarin sodium reacts with the isopropyl alcohol to form a Warfarin sodium.isopropyl alcohol complex which crystallizes and is readily separated from the non-Warfarin impurities.

U.S. Pat. No. 3,192,232 relates to Warfarin known chemically as 3-(alpha-acetonylbenzyl)-4-hydroxy-coumarin and more specifically to improvements in the art and science of making and purifying Warfarin and alkali metal derivatives of Warfarin, e.g. Warfarin sodium, Warfarin potassium, and the like.

U.S. Pat. No. 3,246,013 discloses a process consisting essentially of neutralizing Warfarin in isopropyl alcohol with a compound represented by the formula RONa, where R is selected from the group consisting of hydrogen and alkyl groups such as methyl, ethyl, n-propyl, isopropyl, n-butyl, isobutyl, sec-butyl and tertiary butyl groups, i.e. lower alkyl groups containing 1-4 carbon atoms. The process is carried out by mixing or suspending Warfarin in excess isopropyl alcohol and slowly adding with rapid stirring the RONa compound to the resulting Warfarin-isopropyl alcohol slurry or suspension, warming the resulting reaction mixture, e.g. to 50-80° C., cooling the reaction mixture, e.g. allowing the warm reaction mixture to cool to room temperature, and recovering the crystalline Warfarin sodium.isopropyl alcohol complex after it crystallizes out of the cooled reaction mixture, e.g. by filtration.

U.S. Pat. No. 5,696,274 provides processes which are flexible, cost effective, and commercially viable methods of manufacturing for producing products from 2-hydroxyacetophenone (2-HAP). Of particular interest of the available products are 4-hydroxycoumarin, Warfarin-alkali salt, preferably Warfarin sodium and Warfarin-alkali salt-isopropyl alcohol (2-propanol) complex, more preferably Warfarin-sodium-isopropyl alcohol complex. As is known, these compounds are useful as vitamin K dependent anticoagulants in the treatment of humans and animals. In different doses, they are also useful as a rodenticide. The inventive process involves contacting 2-HAP, carbonate ester and effective base followed by treatment with an unsaturated ketone and phase transfer catalyst to ultimately yield product.

U.S. Pat. No. 6,512,005 describes a procedure for the purification of Warfarin acid. Sodium, potassium and lithium Warfarin salts and the corresponding clathrates are prepared in high, pharmacopeial grade purity and good yields from the pure Warfarin acid and the respective metal salt bases in suitable media.

WO 02/070503 describes an improved procedure for the purification of Warfarin acid. Sodium, potassium and lithium Warfarin salts and the corresponding clathrates are prepared in high, pharmacopeial grade purity and good yields from the pure Warfarin acid and the respective metal salt bases in suitable media. The process for preparing pure Warfarin acid from crude Warfarin acid starts by suspending the crude acid in a water immiscible solvent, extracting the acid into an aqueous solution of dilute base, separating the resulting aqueous phase and diluting it with a lower alkyl alcohol. The aqueous solution is filtered before being diluted with the lower alkyl alcohol. The solution is acidified to a pH of about 2 to 5 using a suitable acid, such as hydrochloric, sulfuric or phosphoric acid. The resulting suspension is stirred at a temperature of from about to 20° C. to about 60° C., cooling the suspension below room temperature, filtering the pure Warfarin acid and drying.

SUMMARY

The present invention relates, at least in part, to crystalline solvate forms of Warfarin potassium, namely polymorphic forms of Warfarin potassium termed herein as APO-I and APO-II and to processes for preparing APO-I and APO-II.

APO-I and APO-II polymorphic forms may provide advantages which may make them chemically and/or polymorphically stable and/or they may have varying solubilities relative to other forms of Warfarin. The molar ratio of solvate molecule to Warfarin is about 0.5:1. For APO-I, the solvate molecule is isopropanol and for APO-II the solvate molecule is ethyl acetate.

Illustrative embodiments of the present invention provide APO-I polymorphic form of Warfarin potassium.

Illustrative embodiments of the present invention provide an APO-I polymorphic form of Warfarin potassium described herein having a powder X-ray diffraction pattern comprising peaks, in terms of degrees 2-theta, at approximately 9.8, 15.3, 21.4, 22.3, 24.2 and 27.5.

Illustrative embodiments of the present invention provide an APO-I polymorphic form of Warfarin potassium described herein having a powder X-ray diffraction pattern comprising peaks, in terms of degrees 2-theta, at approximately 9.8, 13.1, 15.3, 18.3, 19.5, 21.4, 22.3, 24.2 and 27.5.

Illustrative embodiments of the present invention provide an APO-I polymorphic form of Warfarin potassium described herein having a 1% KBr FTIR spectrum comprising peaks, in terms of $cm^{-1}$, at approximately 3454, 1721, 1622, 1600 and 1524

Illustrative embodiments of the present invention provide an APO-I polymorphic form of Warfarin potassium described herein having a DSC thermogram comprising an endothermic peak with a peak onset temperature of approximately 163.3° C. and a peak maximum of approximately 171.6° C.

Illustrative embodiments of the present invention provide an APO-I polymorphic form of Warfarin potassium described herein having a PXRD diffractogram substantially similar to a PXRD diffractogram as depicted in FIG. 1.

Illustrative embodiments of the present invention provide an APO-I polymorphic form of Warfarin potassium described herein having a FTIR spectrum substantially similar to a FTIR spectrum as depicted in FIG. 2.

Illustrative embodiments of the present invention provide an APO-I polymorphic form of Warfarin potassium described herein having a DSC thermogram substantially similar to a DSC thermogram as depicted in FIG. 3.

Illustrative embodiments of the present invention provide APO-II polymorphic form of Warfarin potassium.

Illustrative embodiments of the present invention provide an APO-II polymorphic form of Warfarin potassium described herein having a powder X-ray diffraction pattern comprising peaks, in terms of degrees 2-theta, at approximately 9.7, 14.5, 21.6, 22.1, and 24.7.

Illustrative embodiments of the present invention provide an APO-II polymorphic form of Warfarin potassium described herein having a powder X-ray diffraction pattern comprising peaks, in terms of degrees 2-theta, at approximately 8.5, 9.7, 12.7, 14.5, 18.3, 20.1, 21.6, 22.1, 24.7 and 27.4.

Illustrative embodiments of the present invention provide an APO-II polymorphic form of Warfarin potassium described herein having a 1% KBr FTIR spectrum comprising peaks, in terms of $cm^{-1}$, at approximately 3424, 1721, 1629, 1602 and 1528.

Illustrative embodiments of the present invention provide an APO-II polymorphic form of Warfarin potassium described herein having a DSC thermogram comprising an endothermic peak with a peak onset temperature of approximately 162.9° C. and a peak maximum of approximately 172.3° C.

Illustrative embodiments of the present invention provide an APO-II polymorphic form of Warfarin potassium described herein having a PXRD diffractogram substantially similar to a PXRD diffractogram as depicted in FIG. 4.

Illustrative embodiments of the present invention provide an APO-II polymorphic form of Warfarin potassium described herein having a FTIR spectrum substantially similar to a FTIR spectrum as depicted in FIG. 5.

Illustrative embodiments of the present invention provide an APO-II polymorphic form of Warfarin potassium described herein having a DSC thermogram substantially similar to a DSC thermogram as depicted in FIG. 6.

Illustrative embodiments of the present invention provide a pharmaceutical formulation comprising a polymorphic form of Warfarin potassium described herein and a pharmaceutically acceptable excipient.

Illustrative embodiments of the present invention provide a process for preparing APO-I comprising: I. mixing Warfarin acid in isopropanol thereby forming a Warfarin mixture; II. adding to the Warfarin mixture a potassium base selected from either II-i) KOH, $K_2CO_3$, $KHCO_3$, $K_3PO_4$, KOH in water, $K_2CO_3$ in water, $KHCO_3$ in water, $K_3PO_4$ in water, KOH in ROH, $K_2CO_3$ in ROH, $KHCO_3$ in ROH, $K_3PO_4$ in ROH, and mixtures thereof, wherein R is selected from the group consisting of H and $C_1$-$C_4$ alkyl, or II-ii) KOH, $K_2CO_3$, $KHCO_3$, $K_3PO_4$, KH, $KNH_2$, potassium bis(trimethylsilyl) amide, potassium diisopropylamide and mixtures thereof, thereby forming a potassium Warfarin mixture; III. heating the potassium Warfarin mixture to a temperature in a range of from about 45° C. to about 80° C. thereby forming a first solution; IV. maintaining the first solution at a pH in a range of from about 7.0 to about 10.0 thereby forming a Warfarin potassium isopropanol solution; V. distilling the Warfarin potassium isopropanol solution thereby forming a concentrated Warfarin potassium isopropanol solution; VI. stirring the concentrated Warfarin potassium isopropanol solution at a temperature in a range of from about 5° C. to about 50° C. until precipitation occurs thereby forming a precipitate; and VII. isolating the precipitate thereby isolating APO-I.

Illustrative embodiments of the present invention provide a process described herein wherein the potassium base is KOH in water.

Illustrative embodiments of the present invention provide a process described herein wherein the first solution is maintained at a pH in a range of from about 7.8 to about 8.0.

Illustrative embodiments of the present invention provide a process described herein wherein the distilling occurs under reduced pressure.

Illustrative embodiments of the present invention provide a process described herein wherein the isolating comprises filtering, decanting, centrifugation or drying.

Illustrative embodiments of the present invention provide a process described herein wherein the isolating comprises filtering.

Illustrative embodiments of the present invention provide a process described herein further comprising purifying the Warfarin potassium isopropanol solution by adding charcoal or a slurry of charcoal in isopropanol to the Warfarin potassium isopropanol solution and filtering the Warfarin potassium isopropanol solution.

Illustrative embodiments of the present invention provide a process described herein further comprising adding additional isopropanol to the concentrated Warfarin potassium isopropanol solution prior to stirring and distilling further the Warfarin potassium isopropanol solution to remove water prior to stirring.

Illustrative embodiments of the present invention provide a process described herein further comprising drying APO-I.

Illustrative embodiments of the present invention provide a process for preparing APO-II comprising: i. mixing Warfarin acid in isopropanol thereby forming a Warfarin mixture; ii. adding to the Warfarin mixture a potassium base selected from either ii-i) KOH, $K_2CO_3$, $KHCO_3$, $K_3PO_4$, KOH in water, $K_2CO_3$ in water, $KHCO_3$ in water, $K_3PO_4$ in water, KOH in ROH, $K_2CO_3$ in ROH, $KHCO_3$ in ROH, $K_3PO_4$ in ROH, and mixtures thereof, wherein R is selected from the group consisting of H and $C_1$-$C_4$ alkyl, or ii-ii) KOH, $K_2CO_3$, $KHCO_3$, $K_3PO_4$, KH, $KNH_2$, potassium bis(trimethylsilyl) amide, potassium diisopropylamide and mixtures thereof, thereby forming a potassium Warfarin mixture; iii. heating the potassium Warfarin mixture to a temperature in a range of from about 45° C. to about 80° C. thereby forming a first solution; iv. maintaining the first solution at a pH in a range of from about 7.0 to about 10.0 thereby forming a Warfarin potassium isopropanol solution; v. distilling the Warfarin potassium isopropanol solution thereby forming a concentrated Warfarin potassium isopropanol solution; vi. adding additional isopropanol to the concentrated Warfarin potassium isopropanol solution and distilling further to remove water thereby forming a distilled Warfarin potassium isopropanol solution; vii. distilling the distilled Warfarin potassium isopropanol solution to dryness or near-dryness thereby forming a Warfarin potassium residue; viii. dissolving the Warfarin potassium residue in ethyl acetate thereby forming a Warfarin potassium ethyl acetate solution; ix. stirring the Warfarin potassium ethyl acetate solution at a temperature in a range of from about 5° C. to about 50° C. until precipitation occurs thereby forming a precipitate; and x. isolating the precipitate thereby isolating APO-II.

Illustrative embodiments of the present invention provide a process described herein wherein the potassium base is KOH in water.

Illustrative embodiments of the present invention provide a process described herein wherein the first solution is maintained at a pH in a range of from about 7.8 to about 8.0.

Illustrative embodiments of the present invention provide a process described herein wherein the distilling occurs under reduced pressure.

Illustrative embodiments of the present invention provide a process described herein wherein the isolating comprises filtering, decanting, centrifugation or drying.

Illustrative embodiments of the present invention provide a process described herein wherein the isolating comprises filtering.

Illustrative embodiments of the present invention provide a process described herein further comprising purifying the Warfarin potassium isopropanol solution by adding charcoal or a slurry of charcoal in isopropanol to the Warfarin potassium isopropanol solution and filtering the Warfarin potassium isopropanol solution.

Illustrative embodiments of the present invention provide a process described herein further comprising drying APO-II.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Drawings which illustrate embodiments of the invention are.

DETAILED DESCRIPTION

Figure 1:
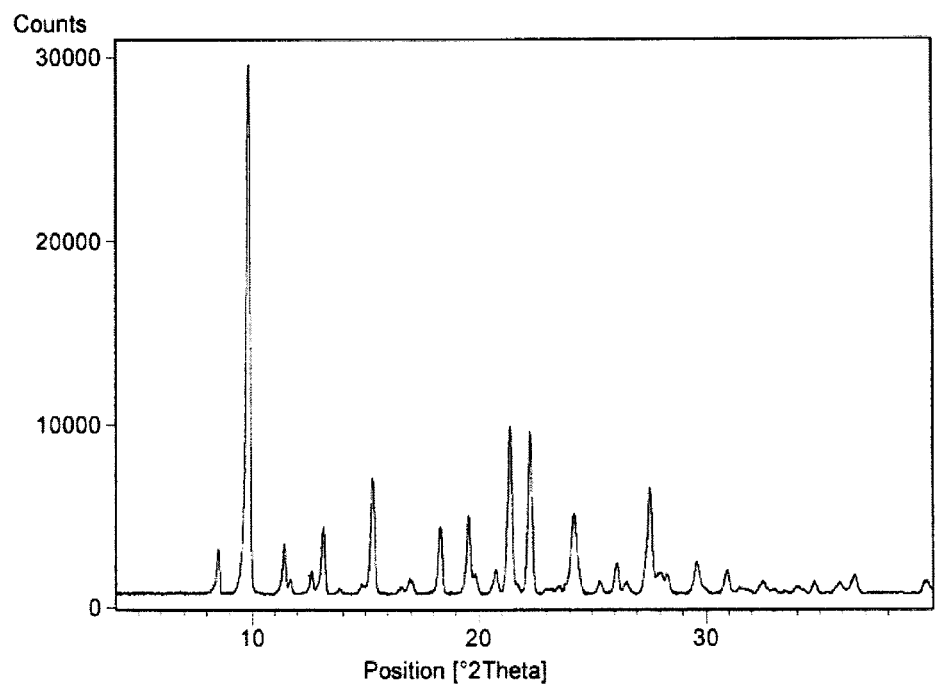
FIG. 1: is a powder X-ray diffraction (PXRD) diffractogram of APO-I.

When used in reference to a diffractogram, a spectrum and/or data presented in a graph, the term "substantially similar" means that the subject diffractogram, spectrum and/or data presented in a graph encompasses all diffractograms, spectra and/or data presented in graphs that vary within acceptable boundaries of experimentation that are known to a person of skill in the art. Such boundaries of experimentation will vary depending on the type of the subject diffractogram, spectrum and/or data presented in a graph, but will nevertheless be known to a person of skill in the art.

When used in reference to a peak in a powder X-ray diffraction (PXRD) diffractogram, the term "approximately" means that the peak may vary by ±0.2 degrees 2-theta of the subject value.

When used in reference to a peak in a Fourier transform infrared (FTIR) spectrum, the term "approximately" means that the peak may vary by ±5 $cm^{-1}$ of the subject value.

When used in reference to a peak in a differential scanning calorimetry (DSC) thermogram, the term "approximately" means that the peak may vary by ±1 degree of the subject value.

As used herein when referring to a diffractogram, spectrum and/or to data presented in a graph, the term "peak" refers to a feature that one skilled in the art would recognize as not attributing to background noise.

Depending on the nature of the methodology applied and the scale selected to display results obtained from an X-ray diffraction analysis, an intensity of a peak obtained may vary quite dramatically. For example, it is possible to obtain a relative peak intensity of 0.01% when analyzing one sample of a substance, but another sample of the same substance may show a much different relative intensity for a peak at the same position. This may be due, in part, to the preferred orientation of the sample and its deviation from the ideal random sample orientation, sample preparation and the methodology applied. Such variations are known and understood by a person of skill in the art.

In an illustrative embodiment, the present invention comprises a crystalline isopropanol solvate form of Warfarin potassium which is a polymorphic form referred to herein as APO-I. APO-I may be characterized by an X-ray powder diffraction pattern comprising peaks, in terms of 2-theta, at approximately 9.8, 15.3, 21.4, 22.3, 24.2 and 27.5. APO-I may be characterized by an X-ray powder diffraction pattern comprising peaks, in terms of 2-theta, at approximately 9.8, 13.1, 15.3, 18.3, 19.5, 21.4, 22.3, 24.2 and 27.5. An illustrative PXRD diffractogram of APO-I is given in FIG. 1. APO-I may also be characterized by a 1% KBr FTIR spectrum comprising peaks, in terms of $cm^{-1}$, at approximately 3454, 1721, 1622, 1600 and 1524. An illustrative FTIR spectrum of APO-I is given in FIG. 2. APO-I may also be characterized by a DSC thermogram comprising an endothermic peak with a peak onset temperature of approximately 163.3° C. and a peak maximum of approximately 171.6° C. An illustrative DSC thermogram of APO-I is given in FIG. 3.

In another illustrative embodiment, the present invention provides a process of preparing APO-I comprising:
  a. mixing Warfarin acid in isopropanol thereby forming a Warfarin mixture;
  b. adding to the Warfarin mixture a potassium base selected from either
    b-i) KOH, $K_2CO_3$, $KHCO_3$, $K_3PO_4$, KOH in water, $K_2CO_3$ in water, $KHCO_3$ in water, $K_3PO_4$ in water, KOH in ROH, $K_2CO_3$ in ROH, $KHCO_3$ in ROH, $K_3PO_4$ in ROH, and mixtures thereof, wherein R is selected from the group consisting of H and $C_1$-$C_4$ alkyl, or
    b-ii) KOH, $K_2CO_3$, $KHCO_3$, $K_3PO_4$, KH, $KNH_2$, potassium bis(trimethylsilyl)amide, potassium diisopropylamide and mixtures thereof,
    thereby forming a potassium Warfarin mixture;
  c. heating the potassium Warfarin mixture to a temperature in a range of from about 45° C. to about 80° C. thereby forming a first solution;
  d. maintaining the first solution at a pH in a range of from about 7.0 to about 10.0 thereby forming a Warfarin potassium isopropanol solution;

e. optionally adding charcoal or a slurry of charcoal in isopropanol to the Warfarin potassium isopropanol solution and filtering;
f. distilling the Warfarin potassium isopropanol solution thereby forming a concentrated Warfarin potassium isopropanol solution, the distilling may optionally be carried out under reduced pressure;
g. optionally adding additional isopropanol and distilling further the Warfarin potassium isopropanol solution to remove water, the distilling may optionally be carried out under reduced pressure;
h. stirring the concentrated Warfarin potassium isopropanol solution at a temperature in a range of from about 5° C. to about 50° C. until precipitation occurs thereby forming a precipitate;
j. isolating the precipitate thereby isolating APO-I; and
k. optionally drying APO-I.

In illustrative embodiments of the present invention, step b comprises forming the potassium Warfarin mixture by adding KOH in water to the Warfarin mixture.

Maintaining the pH of the first solution is typically achieved by adding one or more of KOH, $K_2CO_3$, $KHCO_3$, $K_3PO_4$, KOH in water, $K_2CO_3$ in water, $KHCO_3$ in water, $K_3PO_4$ in water, KOH in ROH, $K_2CO_3$ in ROH, $KHCO_3$ in ROH, $K_3PO_4$ in ROH, and mixtures thereof, wherein R is selected from the group consisting of H and $C_1$-$C_4$ alkyl, KH, $KNH_2$, potassium bis(trimethylsilyl)amide, potassium diisopropylamide and mixtures thereof with the exception that if water or ROH is present, then KH, $KNH_2$, potassium bis(trimethylsilyl)amide, potassium diisopropylamide are not used, in order to increase the pH and/or by adding Warfarin acid to decrease the pH. It may be possible to use other bases and acids, but less of the desired product would be realized.

In illustrative embodiments of the present invention, the first solution is maintained at a pH in a range of from about 7.8 to about 8.0.

In illustrative embodiments of the present invention, the isolating comprises one or more of the following techniques: filtering, decanting, centrifugation and drying. Often the isolating comprises filtering.

Figure 4:
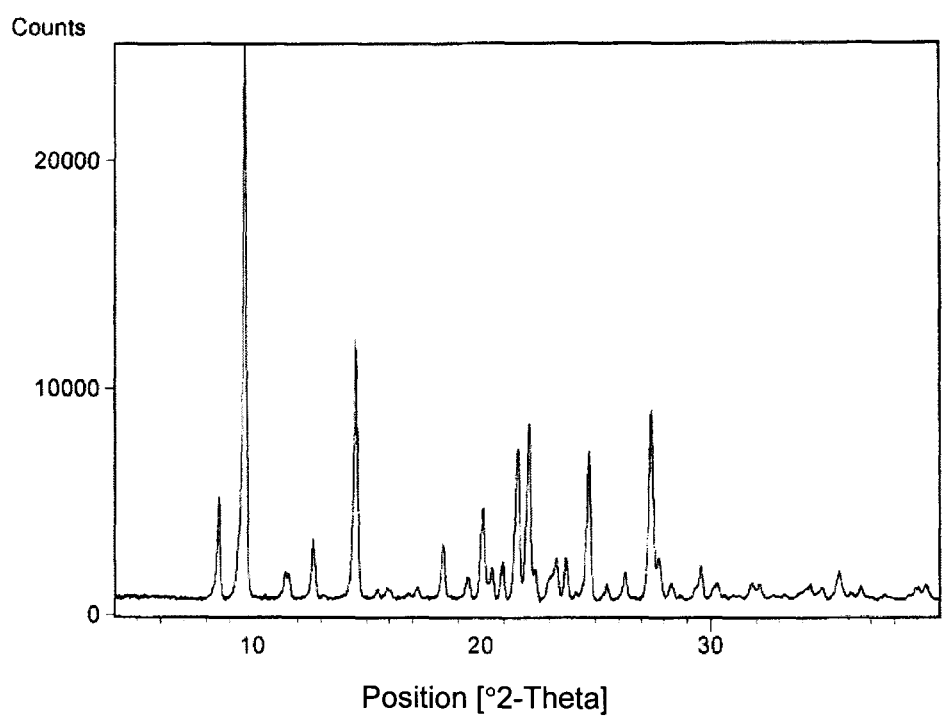
FIG. 4: is a powder X-ray diffraction (PXRD) diffractogram of APO-II.
Figure 5:
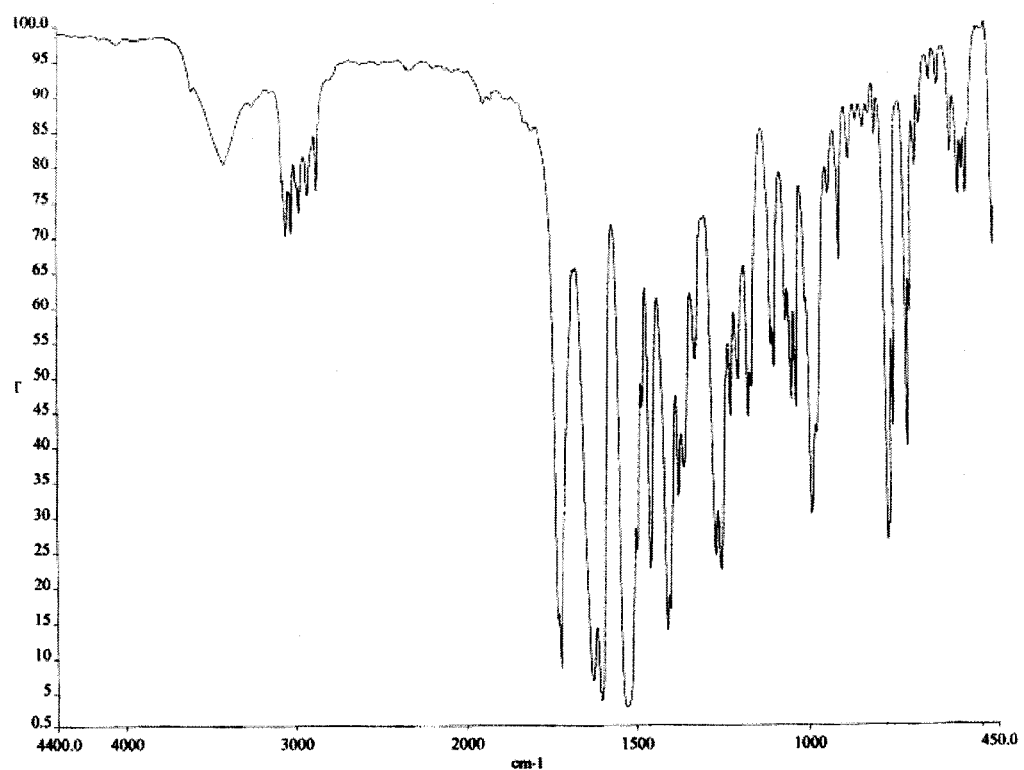
FIG. 5: is a Fourier transform infrared (FTIR) spectrum of APO-II.
Figure 6:
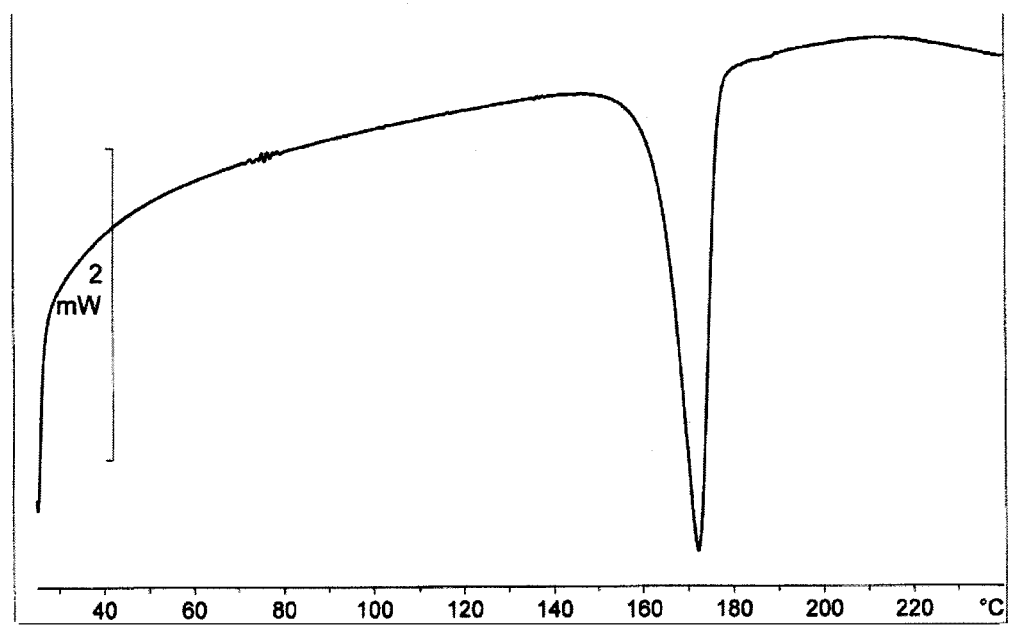
FIG. 6: is a differential scanning calorimetry (DSC) thermogram of APO-II.

In an illustrative embodiment, the present invention comprises a crystalline ethyl acetate solvate form of Warfarin potassium which is a polymorphic form referred to herein as APO-II. APO-II may be characterized by an X-ray powder diffraction pattern comprising peaks, in terms of 2-theta, at approximately 9.7, 14.5, 21.6, 22.1, and 24.7. APO-II may be characterized by an X-ray powder diffraction pattern comprising peaks, in terms of 2-theta, at approximately 8.5, 9.7, 12.7, 14.5, 18.3, 20.1, 21.6, 22.1, 24.7 and 27.4. An illustrative PXRD diffractogram of APO-II is given in FIG. 4. APO-II may also be characterized by a 1% KBr FTIR spectrum comprising peaks, in terms of $cm^{-1}$, at approximately 3424, 1721, 1629, 1602 and 1528. An illustrative FTIR spectrum of APO-II is given in FIG. 5. APO-II may also be characterized by a DSC thermogram comprising an endothermic peak with a peak onset temperature of approximately 162.9° C. and a peak maximum of approximately 172.3° C. An illustrative DSC thermogram of APO-II is given in FIG. 6.

In another illustrative embodiment, the present invention provides a process of preparing APO-II comprising:
A. mixing Warfarin acid in isopropanol thereby forming a Warfarin mixture;
B. adding to the Warfarin mixture a potassium base selected from either
B-i) KOH, $K_2CO_3$, $KHCO_3$, $K_3PO_4$, KOH in water, $K_2CO_3$ in water, $KHCO_3$ in water, $K_3PO_4$ in water, KOH in ROH, $K_2CO_3$ in ROH, $KHCO_3$ in ROH, $K_3PO_4$ in ROH, and mixtures thereof, wherein R is selected from the group consisting of H and $C_1$-$C_4$ alkyl, or
B-ii) KOH, $K_2CO_3$, $KHCO_3$, $K_3PO_4$, KH, $KNH_2$, potassium bis(trimethylsilyl)amide, potassium diisopropylamide and mixtures thereof,
thereby forming a potassium Warfarin mixture;
C. heating the potassium Warfarin mixture to a temperature in a range of from about 45° C. to about 80° C., thereby forming a first solution;
D. maintaining the first solution at a pH in a range of from about 7.0 to 10.0 thereby forming a Warfarin potassium isopropanol solution;
E. optionally adding charcoal or a slurry of charcoal in isopropanol to the Warfarin potassium isopropanol solution and filtering;
F. distilling the Warfarin potassium isopropanol solution, thereby forming a concentrated Warfarin potassium isopropanol solution, the distilling may optionally be carried out under reduced pressure;
G. adding additional isopropanol to the concentrated Warfarin potassium isopropanol solution and distilling further to remove water, thereby forming a distilled Warfarin potassium isopropanol solution, the distilling may optionally be carried out under reduced pressure;
H. distilling the distilled Warfarin potassium isopropanol solution to dryness or near-dryness, thereby forming a Warfarin potassium residue, the distilling may optionally be carried out under reduced pressure;
J. dissolving the Warfarin potassium residue in ethyl acetate thereby forming a Warfarin potassium ethyl acetate solution;
K. stirring the Warfarin potassium ethyl acetate solution at a temperature in a range of from about 5° C. to about 50° C. until precipitation occurs thereby forming a precipitate;
L. isolating the precipitate thereby isolating APO-II; and
M. optionally drying APO-II.

In illustrative embodiments of the present invention step B comprises forming the potassium Warfarin mixture by adding KOH in water to the Warfarin mixture.

Maintaining the pH of the first solution is typically achieved by adding one or more of KOH, $K_2CO_3$, $KHCO_3$, $K_3PO_4$, KOH in water, $K_2CO_3$ in water, $KHCO_3$ in water, $K_3PO_4$ in water, KOH in ROH, $K_2CO_3$ in ROH, $KHCO_3$ in ROH, $K_3PO_4$ in ROH, and mixtures thereof, wherein R is selected from the group consisting of H and $C_1$-$C_4$ alkyl, KH, $KNH_2$, potassium bis(trimethylsilyl)amide, potassium diisopropylamide and mixtures thereof with the exception that if water or ROH is present, then KH, $KNH_2$, potassium bis(trimethylsilyl)amide, potassium diisopropylamide are not used, in order to increase the pH and/or by adding Warfarin acid to decrease the pH. It may be possible to use other bases and acids, but less of the desired product would be realized.

In illustrative embodiments of the present invention, the first solution is maintained at a pH in a range of about 7.8 to about 8.0.

In illustrative embodiments of the present invention, the isolating comprises one or more of filtering, decanting, centrifugation and drying. Often the isolating comprises filtering.

APO-I and APO-II may be formulated into pharmaceutical formulations, typically by adding at least one pharmaceutically acceptable excipient and by using techniques well understood by a person of skill in the art. Many techniques known to one of skill in the art and many pharmaceutically acceptable excipients known to one of skill in the art are described in *Remington: the Science & Practice of Pharmacy* by Alfonso Gennaro, 20th ed., Lippencott Williams & Wilkins, (2000).

The following examples are illustrative of some of the embodiments of the invention described herein. These examples do not limit the spirit or scope of the invention in anyway.

EXAMPLES

Powder X-Ray Diffraction Analysis (PXRD): The data were acquired on a PANanalytical X-Pert Pro MPD diffractometer with fixed divergence slits and an X-Celerator RTMS detector. The diffractometer was configured in Bragg-Brentano geometry; data was collected over a 2-theta range of 4° to 40° using CuKα radiation at a power of 40 mA and 45 kV. CuKβ radiation was removed using a divergent beam nickel filter. A step size of 0.017 degrees was used. A step time of 30 seconds was used. Samples were rotated at 1 Hz to reduce preferred orientation effects. The samples were prepared by the back-loading technique.

Fourier Transform Infrared (FTIR) Analysis: The FTIR spectrum was collected at 4 cm$^{-1}$ resolution using a Perkin Elmer Paragon 1100 single beam FTIR instrument. The samples were intimately mixed in an approximately 1:100 ratio (w/w) with potassium bromide (KBr) using an agate mortar and pestle to a fine consistency; the mixture was compressed in a pellet die at a pressure of 4 to 6 tonnes for a period of time between 2 and 5 minutes. The resulting disk was scanned 4 times versus a collected background. Data was baseline corrected and normalized.

Differential Scanning calorimetry (DSC) Analysis: The DSC thermograms were collected on a Mettler-Toledo 821e instrument. Samples (1 to 5 mg) were weighed into a 40 µL aluminum pan and were crimped closed with an aluminum lid. The samples were analyzed under a flow of nitrogen (ca. 55 mL/min) at a scan rate of 10° C./minute.

Example 1

Preparation of APO-I

A solution of 85% KOH (13.833 g, 209.523 mmol) in water (13 mL) was added to a stirred suspension of Warfarin acid (68 g, 220.6 mmol) in isopropanol (367 mL) at room temperature. The mixture was then heated to 75° C. to obtain a solution. A pH of 7.8 to 8.0 was maintained by adding small amounts of either an aqueous solution of KOH or Warfarin acid, as required. Activated charcoal (3.4 g, 5.0 wt %) was charged and the mixture was heated at 75° C. for 8 h, followed by filtration over Celite™ under nitrogen. The filtrate was concentrated on a rotary evaporator (45 to 50° C.) to ca. 300 mL. Water in the concentrate was azeotropically removed by addition and evaporation of isopropanol (3×200 mL). The mixture was then cooled to room temperature and stirred at that temperature for 20 h. The resulting suspension was filtered under nitrogen and the solid was washed with isopropanol (3×70 mL). The white solid was dried under vacuum at 50° C. for 24 h to obtain the product (67.1 g; 81%) as a white crystalline solid. The molar ratio between Warfarin and isopropanol was about 1:0.5.

Example 2

Preparation of APO-II

A solution of 85% KOH (6.92 g, 104.762 mmol) in water (6.5 mL) was added to a stirred suspension of Warfarin acid (34 g, 110.3 mmol) in isopropanol (185 mL) at room temperature. The mixture was then heated to 75° C. to obtain a solution. A pH of 7.8 to 8.0 was maintained by adding small amounts of either an aqueous solution of KOH or Warfarin acid, as required. Activated charcoal (1.7 g, 5.0 wt %) was charged and the mixture was heated at 75° C. for 2 h, followed by filtration over Celite™ under nitrogen. The filtrate was concentrated on a rotary evaporator (45 to 50° C.) to ca. 150 mL. Water in the concentrate was azeotropically removed by addition and evaporation of isopropanol (3×100 mL). From the resulting solution, 10 mL of aliquot was concentrated on a rotary evaporator (45 to 50° C.) and dried under vacuum for 10 min. The resulting gummy mass was dissolved in ethyl acetate (8 mL) and stirred at room temperature for 24 h. The resulting suspension was filtered under nitrogen and the solid was washed with ethyl acetate (2×5 mL). The white solid was dried under vacuum at 50° C. for 24 h to obtain the product (2.91 g) as a white crystalline solid. The molar ratio between Warfarin and ethyl acetate was about 1:0.5.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. Furthermore, numeric ranges are provided so that the range of values is recited in addition to the individual values within the recited range being specifically recited in the absence of the range. The word "comprising" is used herein as an open-ended term, substantially equivalent to the phrase "including, but not limited to", and the word "comprises" has a corresponding meaning. As used herein, the singular forms "a", "an" and "the" include plural references unless the context clearly dictates otherwise. Thus, for example, reference to "a thing" includes more than one such thing. Citation of references herein is not an admission that such references are prior art to the present invention. Furthermore, material appearing in the background section of the specification is not an admission that such material is prior art to the invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings.

What is claimed is:

1. APO-I polymorphic form of Warfarin potassium having a powder X-ray diffraction pattern comprising peaks, in terms of degrees 2-theta, at approximately 9.8, 15.3, 21.4, 22.3, 24.2 and 27.5.

2. The APO-I polymorphic form of Warfarin potassium of claim 1 having a powder X-ray diffraction pattern comprising peaks, in terms of degrees 2-theta, at approximately 9.8, 13.1, 15.3, 18.3, 19.5, 21.4, 22.3, 24.2 and 27.5.

3. The APO-I polymorphic form of Warfarin potassium of claim 2 having a 1% KBr FTIR spectrum comprising peaks, in terms of cm$^{-1}$, at approximately 3454, 1721, 1622, 1600 and 1524.

4. The APO-I polymorphic form of Warfarin potassium of claim 2 having a DSC thermogram comprising an endothermic peak with a peak onset temperature of approximately 163.3° C. and a peak maximum of approximately 171.6° C.

5. The APO-I polymorphic form of Warfarin potassium of claim 1 having a PXRD diffractogram substantially similar to a PXRD diffractogram as depicted in FIG. 1.

Figure 2:
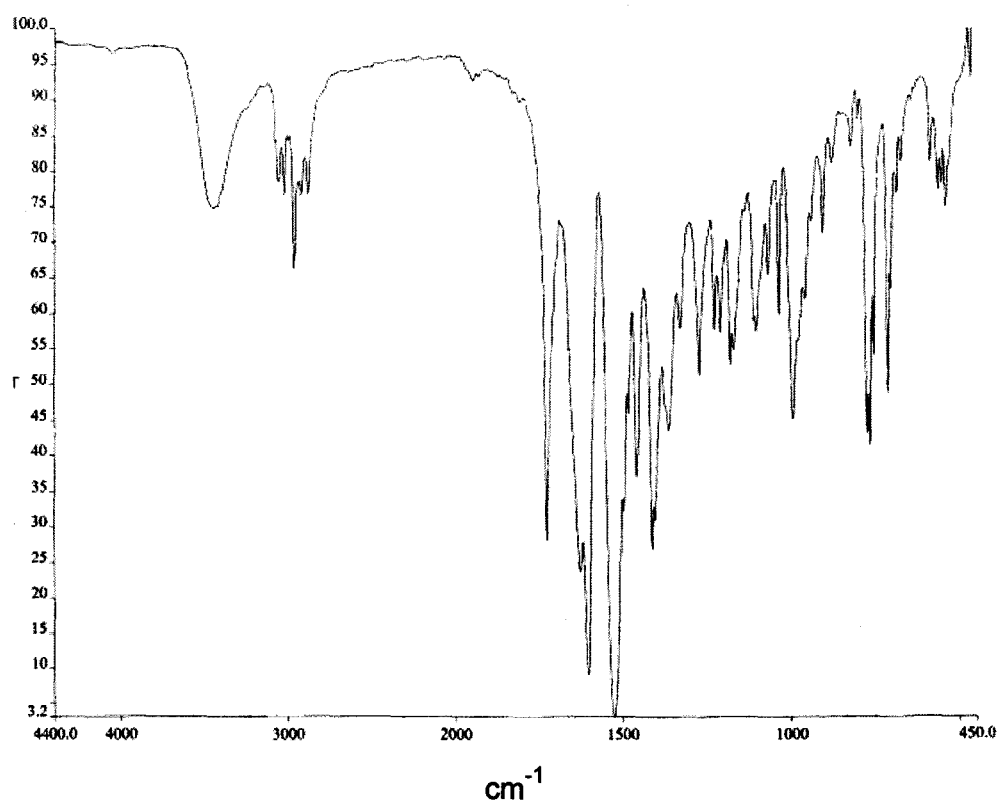
FIG. 2: is a Fourier transform infrared (FTIR) spectrum of APO-I.

6. The APO-I polymorphic form of Warfarin potassium of claim 2 having a FTIR spectrum substantially similar to a FTIR spectrum as depicted in FIG. 2.

Figure 3:
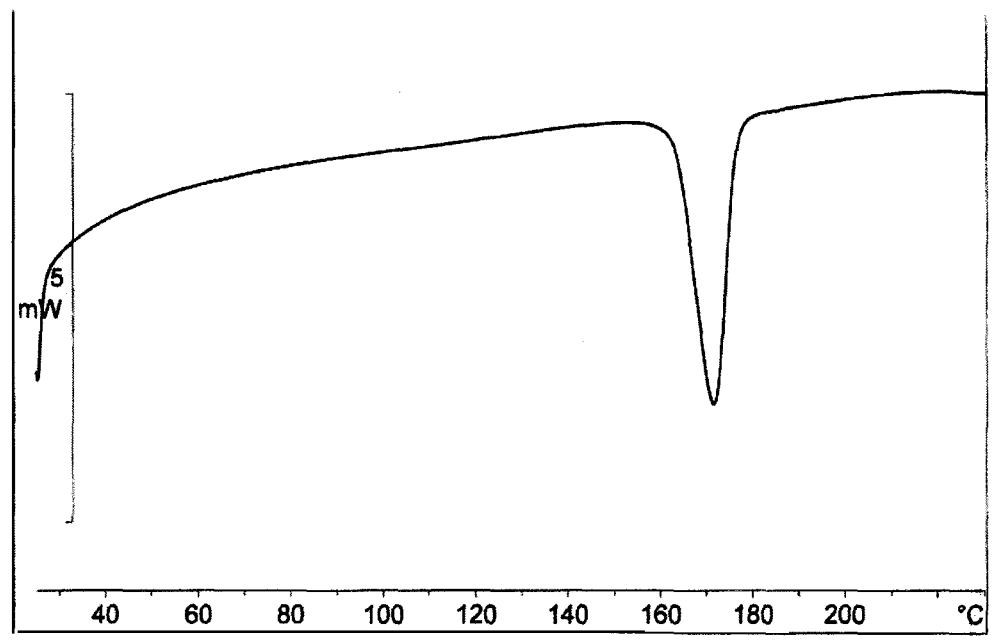
FIG. 3: is a differential scanning calorimetry (DSC) thermogram of APO-I.

7. The APO-I polymorphic form of Warfarin potassium of claim 2 having a DSC thermogram substantially similar to a DSC thermogram as depicted in FIG. 3.

\* \* \* \* \*